US009192787B2

(12) United States Patent
Dessy et al.

(10) Patent No.: US 9,192,787 B2
(45) Date of Patent: Nov. 24, 2015

(54) APPARATUS AND METHOD FOR HADRON BEAM VERIFICATION

(71) Applicant: Ion Beam Applications S.A., Louvain-la-Neuve (BE)

(72) Inventors: Frédéric Dessy, Binche (BE); Yves Claereboudt, Nil-Saint-Vincent (BE)

(73) Assignee: Ion Beam Applications S.A., Louvin-la-Neuve (BE)

( * ) Notice: Subject to any disclaimer, the term of this patent is extended or adjusted under 35 U.S.C. 154(b) by 0 days.

(21) Appl. No.: 14/397,062

(22) PCT Filed: Apr. 24, 2013

(86) PCT No.: PCT/EP2013/058552
§ 371 (c)(1),
(2) Date: Oct. 24, 2014

(87) PCT Pub. No.: WO2013/160379
PCT Pub. Date: Oct. 31, 2013

(65) Prior Publication Data
US 2015/0141732 A1    May 21, 2015

(30) Foreign Application Priority Data

Apr. 25, 2012  (EP) .................................... 12165578
Jul. 19, 2012   (EP) .................................... 12177144

(51) Int. Cl.
*G21K 5/04*       (2006.01)
*A61N 5/10*       (2006.01)

(52) U.S. Cl.
CPC ............ *A61N 5/1049* (2013.01); *A61N 5/1071* (2013.01); *A61N 5/1075* (2013.01); *A61N5/1078* (2013.01); *A61N 2005/1061* (2013.01); *A61N 2005/1076* (2013.01); *A61N 2005/1087* (2013.01)

(58) Field of Classification Search
USPC ........ 250/396 R, 397, 396 ML, 492.1, 492.3; 600/1
See application file for complete search history.

(56) References Cited

U.S. PATENT DOCUMENTS

| 2006/0226372 | A1* | 10/2006 | Yanagisawa et al. ..... 250/396 R |
| 2007/0252093 | A1* | 11/2007 | Fujimaki et al. ........... 250/492.3 |
| 2008/0078955 | A1* | 4/2008  | Graf et al. ................. 250/492.21 |
| 2009/0283702 | A1* | 11/2009 | Umezawa et al. ......... 250/492.3 |

FOREIGN PATENT DOCUMENTS

EP        2 422 847 A1    2/2012

OTHER PUBLICATIONS

International Search Report and Written Opinion, International Patent Application No. PCT/EP2013/058552, completion date Jun. 4, 2013, 9 pages.

* cited by examiner

*Primary Examiner* — Nicole Ippolito
(74) *Attorney, Agent, or Firm* — Fitch, Even, Tabin & Flannery LLP

(57) ABSTRACT

The present invention is related to an apparatus and method for hadron beam verification. The apparatus allows to verify a number of different characteristics in a brief time span. The apparatus comprises at least one main degrader element and associated therewith a multiple thickness degrader element. The latter may comprise a number of patches of beam degrading material, the patches having constant but mutually different thicknesses. Alternatively, it may be a wedge-shaped element. By aiming a pencil beam at the various thicknesses, data points can be obtained which allow to make an estimation of the beam range. In addition to this, the apparatus comprises a zone where no degrader material is present, and where a measurement of the spot size can be obtained, without moving or replacing the apparatus.

19 Claims, 10 Drawing Sheets

FIG. 3
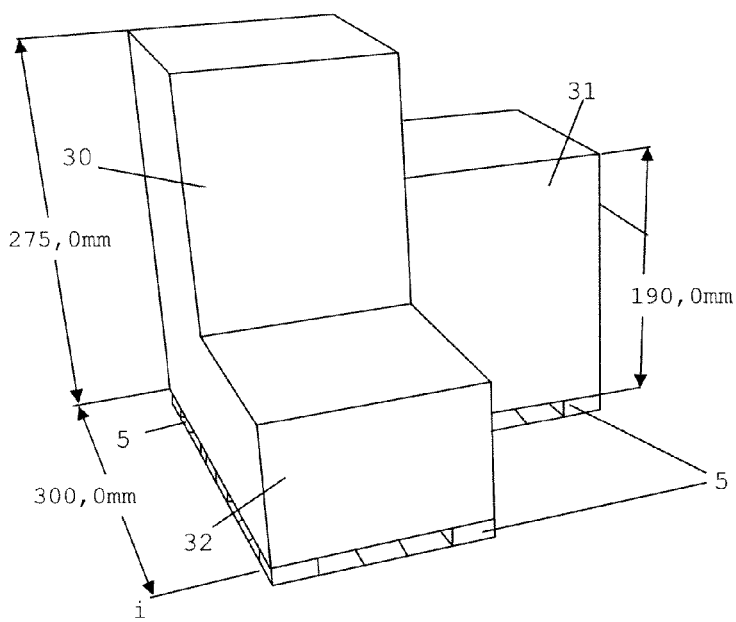
FIG. 4
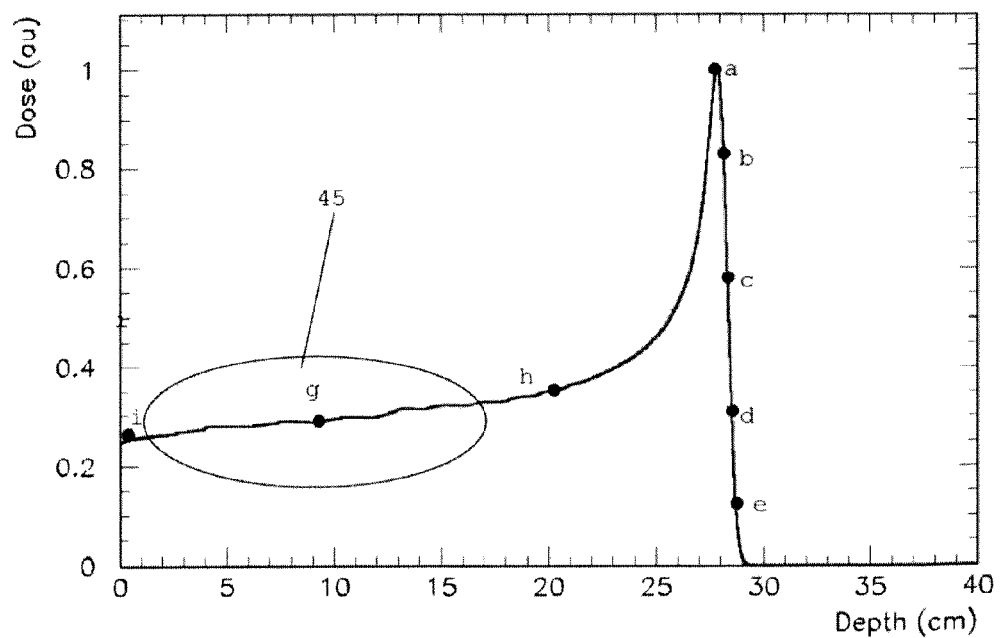
FIG. 5

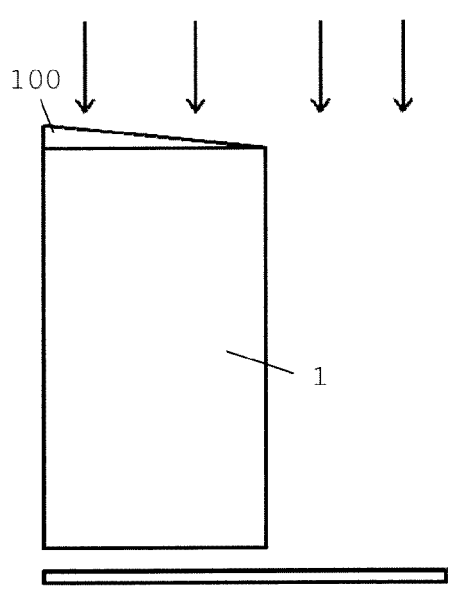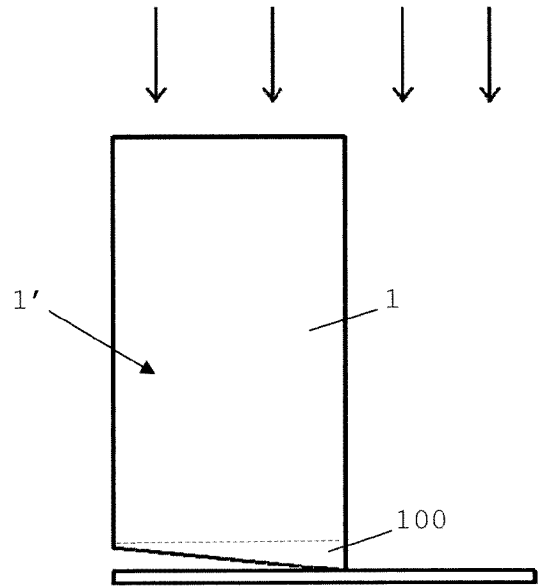
FIG. 8     FIG. 9
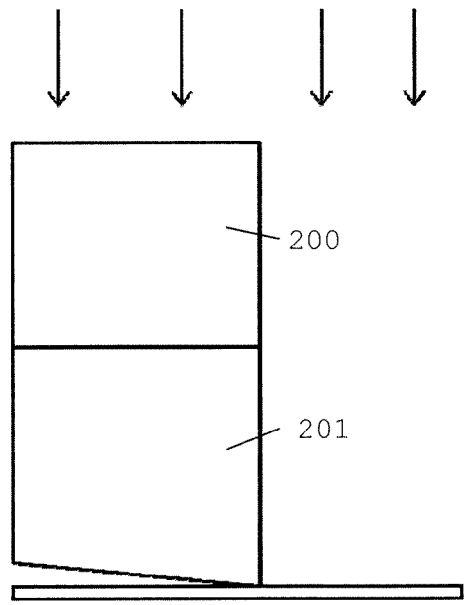
FIG. 10

APPARATUS AND METHOD FOR HADRON BEAM VERIFICATION

CROSS REFERENCE TO RELATED APPLICATIONS

This is a U.S. national phase application of International Application No. PCT/EP2013/058552, filed Apr. 24, 2013, designating the United States and claiming priority to European Patent Application No. 12165578.1, filed Apr. 25, 2012, and European Patent Application No. 12177144.8, filed Jul. 19, 2012, which are incorporated herein by reference in their entireties.

FIELD OF THE INVENTION

The invention is related to the field of charged Hadron therapy. More particularly, the invention is related to the verification of a hadron beam used in the pencil beam scanning technique.

STATE OF THE ART

In current proton beam facilities, the Pencil beam scanning technique (PBS) involves the irradiation of separate spots in a target, each spot having a predefined position and depth, with a pre-defined dose being prescribed for each spot. In each treatment room of the facility, various characteristics of the delivered beam are subjected to a daily verification routine. These characteristics are:

Beam range: the position of the Bragg peak at a given beam energy in a given target, measured usually with a water phantom or multi-layer ionization chamber, spot position and spot size, measured usually by a suitable 2D-detector, for example an array of ionization chambers or a scintillator screen equipped with a CCD camera, the deposited dose, measured usually by an absolute ionization chamber, for checking the output factor of the irradiation installation.

Each of these characteristics is commonly measured at a number of distinct beam energy levels, by a separate measurement device. The time needed to complete a verification routine is therefore at least 60 minutes. Such long verification times are reducing the efficiency of the treatment facility in terms of the number of treatments that can be performed per day.

Document EP2422847 is related to a dosimetry device for verification of a radiation beam in standard and conformal radiation therapy, and in particular in IMRT (Intensity Modulated Radiation Therapy). The device comprises an active area comprising lines of radiation detectors, and a build-up plate provided with degraders of different thicknesses. This device is not suitable for measuring a beam range of a particle beam, because the thickness of the build-up plate is not adapted to the position of a Bragg peak produced by a hadron beam of a predefined energy.

SUMMARY OF THE INVENTION

The invention is related to an apparatus for hadron beam verification as disclosed in the appended claims. The apparatus of the invention allows the verification of at least the beam range and the spot size and spot position without replacing the apparatus or changing its position. Particular embodiments of the apparatus allow to perform all of the above-described verifications within a timeframe of about 15 minutes. The apparatus furthermore allows to make an estimation of the beam range with a high resolution of the data points on which said estimation is based.

The invention is thus firstly related to an apparatus for verification of characteristics of pencil beams produced by a hadron beam irradiation installation, comprising:

A main degrader element, comprising two mutually parallel surfaces, the distance between said surfaces defining the thickness of said main degrader element, Associated with said main degrader element, a multiple thickness degrader element, comprising a plurality of degrader portions of different thicknesses, 'associated with' meaning that each of said portions is facing a different portion of the cross-section of one of said mutually parallel surfaces, A two-dimensional detection means, suitable for detecting a deposited dose or a signal representative thereof or proportional thereto, said detection means having a first portion associated with said main and multiple thickness degrader elements, 'associated with' meaning that said first portion is configured to detect pencil beams which have passed through said main degrader element and said multiple thickness degrader element, wherein:

the thickness of said main degrader element and the thickness of said degrader portions of the multiple thickness degrader element are designed with respect to a pre-defined beam energy, so as to obtain—through said first portion of the detection means—a plurality of data points in the vicinity of a Bragg peak appearing when a beam having said beam energy passes through said main degrader element, said two-dimensional detection means comprises a second portion configured to detect pencil beams that have not passed through said degrader elements.

According to an embodiment, said degrader portions are formed by a plurality of degrader patches of different thicknesses, each patch having a constant thickness, said patches being positioned parallel to said mutually parallel surfaces of the main degrader element. The multiple thickness degrader element may further comprise at least one area where no degrader patch is present.

According to an embodiment, all of said degrader patches, having a first and a second surface with said thickness being the distance between said surfaces, are arranged so that all of the first surfaces of each patch are in a single plane and all of the second surfaces of each patch are extending away from said plane.

According to an embodiment, the main degrader element and the multiple thickness degrader element have the same rectangular cross-section along the direction of said mutually parallel surfaces, and said patches have rectangular sections along said direction.

According to another embodiment, said multiple thickness degrader element is a wedge-shaped degrader element, said degrader portions being formed by cross-sections of the wedge-shaped element that have different thicknesses.

An apparatus according to the invention may comprise a plurality of main degrader elements of different thicknesses, each main degrader element being associated with a multiple thickness degrader element, and wherein said two-dimensional detection means comprises portions associated with each of said main degrader elements, and further comprising said second portion configured to detect pencil beams that have not passed through any of said degrader elements, wherein the thickness of each main degrader element is associated with a different pre-defined beam energy.

According to an embodiment, said main degrader element or at least one of said main degrader elements comprises an area wherein a detector can be mounted suitable for determining the absolute dose deposited by a pencil beam aimed at said detector, and wherein said detector is positioned in the plateau area of the Bragg peak occurring in said main degrader element.

An apparatus according to the invention may further comprise a plurality of X-ray targets suitable for establishing a reference position of the apparatus.

According to another embodiment, the apparatus of the invention further comprises data treatment means and data representation means, suitable for receiving and treating signals obtained from the 2D-detector and to derive and present on the basis of those signals at least the following data:
  the beam range, and
  the spot size or a parameter representative of said size.

According to an embodiment, the main degrader element(s) is (are) formed from a plurality of separate layers assembled together by suitable assembly means. Some of the layers may be common to two or more of the main degrader elements.

According to an embodiment, the main degrader element or elements is or are built up from separate layers, i.e. the main degrader element(s) is(are) modularly built, and can thus be easily assembled into a plurality of configurations. Layers that are common to a plurality of main degrader elements may be produced as integral pieces. One of said layers may comprise an area wherein a detector can be mounted suitable for determining the absolute dose deposited by a pencil beam aimed at said detector.

The invention is equally related to a hadron therapy system for irradiating a target with a hadron pencil beam, said hadron therapy system comprising:
  A hadron beam generator for generating a hadron pencil beam;
  a scanning device for scanning said target with said hadron pencil beam, said scanning device comprising:
    one or more scanning magnets configured for scanning the hadron pencil beam over an X-Y scanning plane, said scanning X-Y plane being perpendicular to an axis Z corresponding to a central beam path, said central beam path being the trajectory of the hadron pencil beam when all of said one or more scanning magnets are not energized;
    scanning control means configured for scanning the hadron pencil beam by sequentially moving the particle beam to multiple scanning positions situated in said X-Y scanning plane;
  an apparatus for verification of characteristics of said pencil beam according to the invention, said apparatus being located such that said parallel surfaces of said main degrader element are essentially perpendicular to said axis Z.

According to an embodiment, each of said scanning positions is correlated either to one of said plurality of degrader portions or it is correlated to a location in said second portion of said two-dimensional detector.

The invention is equally related to a method for verifying characteristics of a pencil beam irradiation procedure, said method comprising the step of:
  Positioning the apparatus the invention at a predefined location with respect to a hadron beam irradiation nozzle, so that a pencil beam may be directed at the mutually parallel planes of the main degrader element,
  Setting the hadron beam irradiation installation for delivering a pencil beam having an energy corresponding to the pre-defined energy for which the thickness of the main degrader element and the thickness of the degrader portions are designed,
  Producing said pencil beam,
  Sending said pencil beam in the direction of at least two of said plurality of degrader portions of different thickness, and detecting with the first portion of said two-dimensional detection means a plurality of data points in the vicinity of a Bragg peak appearing as a consequence of said beam passing through said main degrader element,
  Sending said pencil beam in the direction of one or more predefined spot locations on the second portion of the two-dimensional detection means,
  Deriving from the obtained data at least:
    the beam range, and
    the spot size or a parameter representative of said size.
The beam range is preferably obtained by an estimation of the Bragg peak shape on the basis of a sufficiently high number of said data points.

In the method of the invention, the step of positioning the apparatus may include placing the apparatus on a predefined position of a patient couch of a hadron therapy treatment room, and positioning the patient couch.

The method of the invention may further comprise the step of taking an X-ray image of the apparatus and positioning the apparatus by comparing the position of X-ray targets in said X-ray image to a reference image.

BRIEF DESCRIPTION OF THE FIGURES

FIG. 4 shows an apparatus according to the invention, configured for verifying beam characteristics at three distinct beam energy levels.

FIG. 5 is a graph of the Bragg peak and data points obtained using the apparatus of FIG. 4.

FIGS. 8, 9 and 10 illustrate variations of the structure of the apparatus of the invention.

DETAILED DESCRIPTION OF THE INVENTION

The following description refers to a device for proton beam verification. The device is however suitable for verification of any other type of hadron beam (ion beam e.g.). FIG.

Figure 1A:
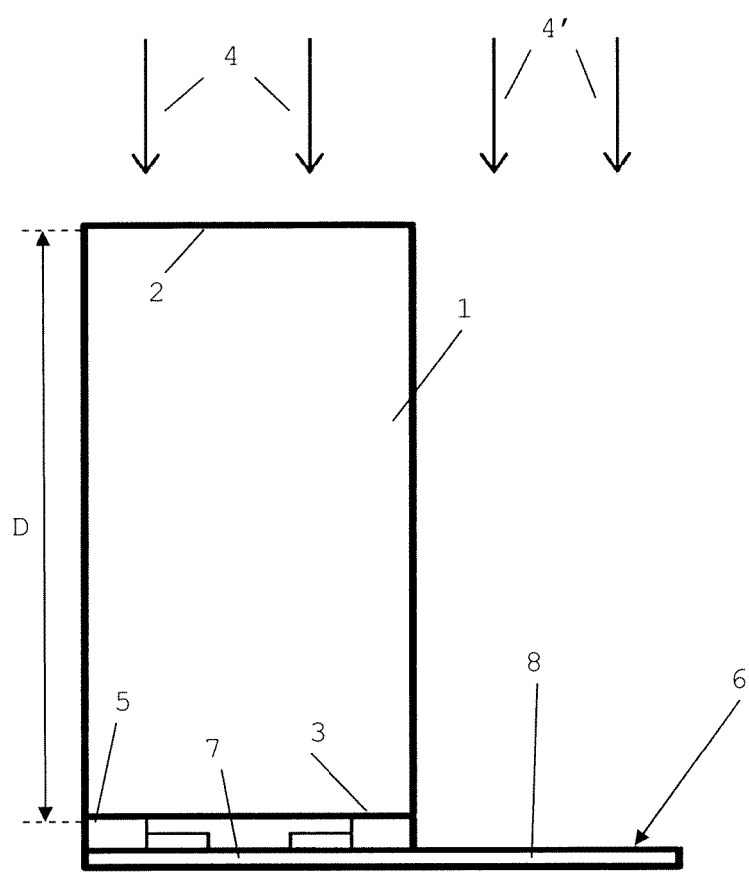
FIG. 1a is a schematic view of the basic components in a first embodiment of an apparatus of the invention.

1 is a schematic representation of a device according to a first embodiment of the invention. It comprises three basic components:
- a main degrader element 1: this is a volume of material with known proton beam energy degrading characteristics. The main degrader element has mutually parallel surfaces 2 and 3. The main degrader element is suitable for being positioned with respect to a pencil beam irradiation installation so that pencil beams may be aimed at the parallel surfaces 2 and 3 (i.e. the beam passes through the degrader element from one surface to the other; possibly the beam is perpendicular to both surfaces). The main degrader element 1 has a predefined thickness D. Preferably the degrader element 1 is a rectangular block of PMMA or another suitable material with a known water-equivalent thickness. Alternatively, the degrader element is a volume of water.
- A multiple thickness degrader element 5: in the particular embodiment of FIG. 1, this is an element comprising a plurality of degrader patches of different thickness, preferably of the same material as the main degrader element 1, wherein each patch is positioned so that it faces a different portion of the main degrader element's surface 3. In other words, the patches do not overlap each other in a plane parallel to the surfaces 2 and 3. According to the preferred embodiment, the patches are arranged on a single flat surface that is parallel to the main degrader's parallel surfaces 2 and 3.
- A two-dimensional detection means 6 (hereafter referred to as '2D detector'), comprising a first portion 7 configured to detect the deposited dose or a signal representative of or proportional to said dose, of pencil beams 4 passing through the main degrader element 1 and the multiple thickness degrader element 2, and a second portion 8 configured to detect beam characteristics of pencil beams 4' that are not passing through the degrader elements 1 and 2. The 2D-detector can be an array of ionization chambers or a scintillator screen or liquid scintillator, equipped with a CCD camera, as known in the art. The apparatus of the invention may comprise or be connected to data treatment means and to data representation means, suitable for receiving and treating signals obtained from the 2D-detector and to derive and present on the basis of those signals at least the following data:
  - An estimation of the beam range (obtained through the portion 7 of the 2D detector), and
  - a representation of the spot size and possibly also the spot position and/or the spot fluence, or of a parameter representative thereof (obtained through the portion 8 of the 2D detector)

Figure 1B:
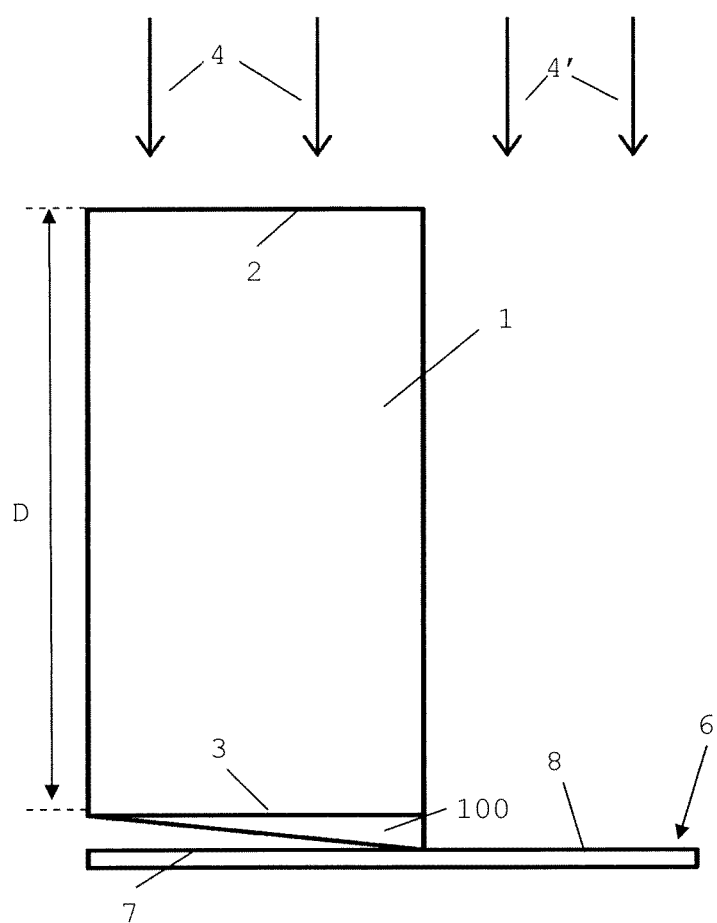
FIG. 1b illustrates a second embodiment.

According to a second embodiment, the multiple thickness degrader element is a wedge degrader element 100, as illustrated in FIG. 1b. The wedge element has a continuously changing thickness from one side to the other. The wedge element is therefore another example of the multiple thickness degrader element referred to in the appended claims. In the wedge element, the degrader portions referred to in the claims are formed by cross-sections of different thickness.

The main degrader element 1 has a thickness D that is designed with respect to a pre-defined proton beam energy. For this energy the predicted maximum of the Bragg peak (based on the beam energy and degrader material characteristics) is situated approximately at the end plane of the main degrader 1, and preferably downstream of said end plane (seen in the direction of the beam). When the multiple thickness element 5 or the wedge element 100 is placed after the main degrader element, preferably in contact with said element, i.e. forming an extension of said element, a measurement of the dose deposited by pencil beams aimed at the various patches 10 or at sections of the wedge 100 having various thicknesses allows to measure the shape of the actual Bragg peak. Due to the presence of the main degrader element, any of the patches 10 or sections of the wedge elements allows to obtain a data point that is close to the maximum of the Bragg peak. The apparatus of the invention thus allows to obtain a high number of data points in the vicinity of said maximum, and hence a high resolution of said data points, leading to a high accuracy of the estimated beam range.

The multiple thickness patch element 5 and the wedge element 100 are representations of the multiple thickness degrader element cited in the appended claims. Other representations of such an element may be imagined, e.g. a wedge with a non-linearly changing thickness, or a combination of wedge-shaped areas and constant-thickness areas within one multiple thickness degrader element. In any case, the main degrader element and the multiple thickness degrader element are configured so that a pencil beam directed at the apparatus can pass through the parallel surfaces (2,3) of the main element, and through one of the degrader portions of the multiple thickness element have mutually different thicknesses. As explained later, the main and multiple thickness degrader elements need not be physically separate elements, but they may be integrally formed in one or more degrader elements that encompass(ses) both the functions of the main degrader element and the multiple thickness degrader element. A feature that is also characteristic to a device according to the invention is that the thickness of the main degrader element is significantly higher than the highest thickness in the multiple thickness degrader element, for example the thickness of the thickest patch in the embodiment with multiple patches, or the thickest cross-section in the embodiment with the wedge element. This can be expressed in terms of the ratio of the thickness of the main degrader element to the highest thickness of the multiple thickness degrader element. Said ratio is preferably higher than 5. According to other embodiments, the ratio is higher than 10 or higher than 15. According to another embodiment, the ratio is between any of the previous values and an upper value of 30. These embodiments cover the most useful range of hadron beam energies.

Figure 2:
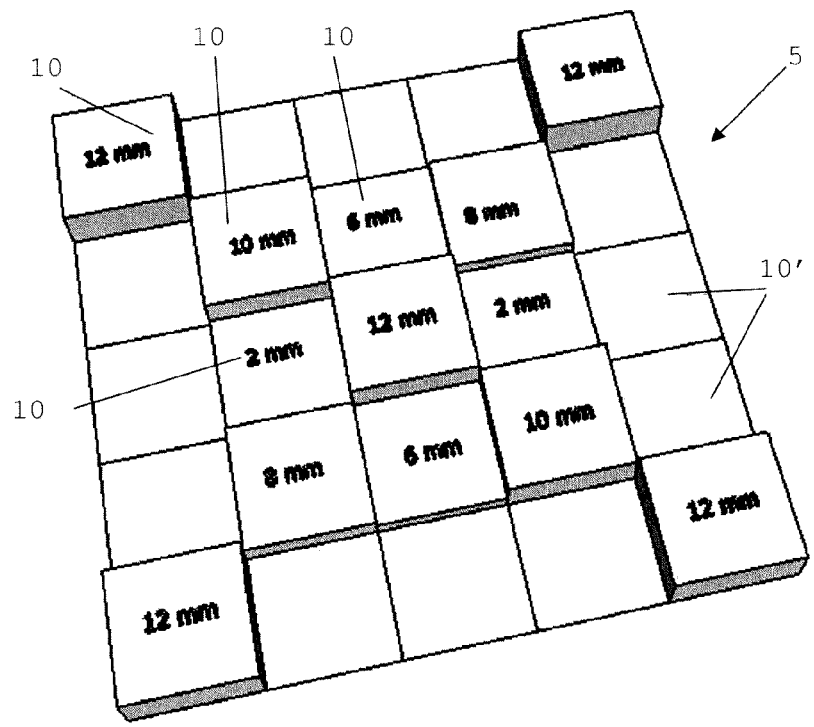
FIG. 2 shows an embodiment of one particular component, the multiple thickness degrader element, in an apparatus of the invention.
Figure 3:
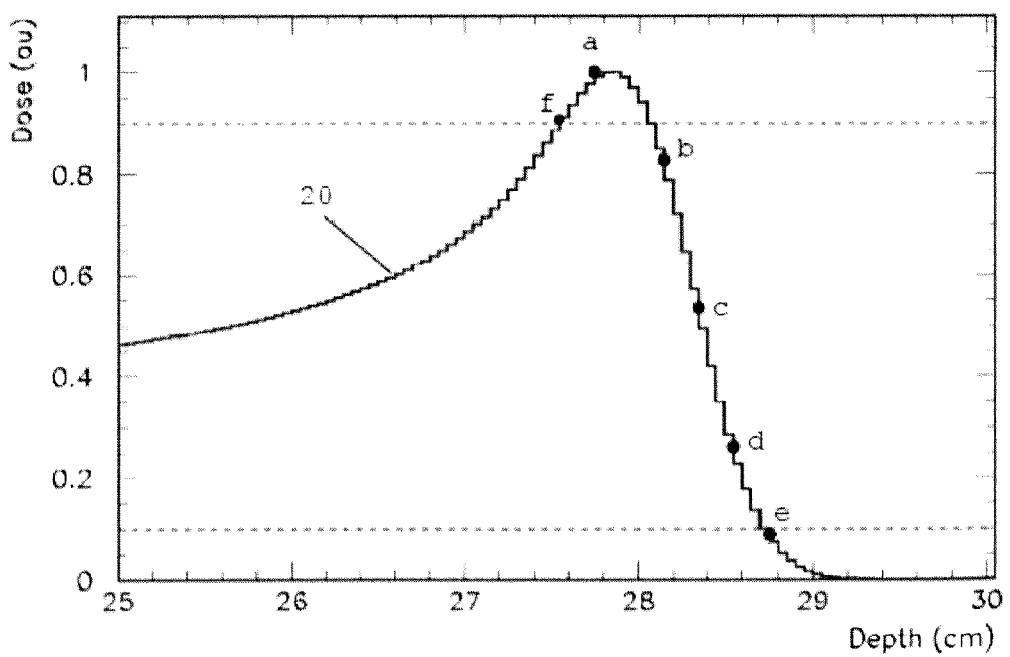
FIG. 3 illustrates the data points measured using an apparatus of the invention, for determining the beam range, and how these data points allow to determine the beam range.

A preferred embodiment of the multiple thickness degrader element 5 is shown in FIG. 2. It comprises a plurality of square patches 10 of various thicknesses, attached to the same flat sheet 6, while a number of areas 10' of the sheet are not occupied by these patches. The patches 10 are made of the same material as the degrader element 1, for example PMMA. The sheet 6 has negligible thickness compared to the patches in terms of acting as a degrader element. The sheet could for example be made of a thin layer of PMMA. Alternatively, the main degrader 1 and the multiple thickness degrader element 5 (i.e. the patches 10) could be made of a single piece of material. In the example of FIG. 3, the device comprises 25 square areas of 3×3 cm$^2$, occupied by 5 12 mm-patches, 2 10 mm-patches, 2 8 mm-patches, 2 6-mm patches and 2 2-mm patches. The remaining 9 squares are empty.

FIG. 3 shows the result of a simulation of the system, for a main degrader element 1 of thickness D=275 mm and square cross section of 15×15 cm$^2$, irradiated by a pencil beam at 210 MeV, with the multiple thickness degrader element 5 of FIG. 2 placed directly behind the main degrader element 1. The curve 20 is the 'actual' Bragg peak. The beam energy in this example is chosen such that the 10% dose level of the Bragg peak is located at a depth corresponding to the maximum water equivalent thickness of the apparatus of the invention.

In this example, the maximum water equivalent thickness is 287 mm which is the sum of the main degrader water equivalent thickness of 275 mm plus the water equivalent thickness of the patch having the largest thickness (i.e. 12 mm). The term 'water equivalent thickness' is used in the above, which is not necessarily the same as the real thickness. When the main degrader element and the patches are made from PMMA, the water equivalent thickness is essentially the same as the real thickness. The corresponding beam energy as used for the simulation was 210 MeV. The data points a to e are simulations of the measured dose, as measured by the device of FIG. 1, when a pencil beam is aimed at patches of various thickness. These data points a to e are measured by the detectors of the 2D-detector 6 that are facing the following patches:

Point a: 2 mm patches
Point b: 6 mm patches
Point c: 8 mm patches
Point d: 10 mm patches
Point e: 12 mm patches Preferably, another data point f is obtained by measuring the dose at one of the empty areas 10'. It is clear that the measurement of the points a to e alone allows to reconstruct the actual Bragg peak and to derive from that an estimation of the beam range (most often defined as the position at which the dose reaches 90% of the maximum dose level, but other definitions can be used within the context of this invention). The wedge element 100 allows to obtain the same data points a to e by subsequently directing a pencil beam at sections of the wedge that have a thickness of 2 mm, 6 mm, 8 mm, 10 and 12 mm. The wedge element could also comprise an area with zero thickness in order to obtain the data point f.

The multiple thickness degrader element shown in FIG. 2 has several groups of patches of the same thickness. This allows to repeat a measurement on the same patch thickness at various locations over the cross-section. In this way, the measurement can be optimized statistically. It is however not required for the multiple thickness degrader element to have more than one patch of the same thickness, nor is it necessary to have as many different thicknesses as shown in the example of FIG. 2. The minimum number of patches of different thickness required to be able to estimate the beam range is two, provided that at least one empty area 10' is present also. If no empty area is present, the minimum number of patches is three.

Returning to FIGS. 1a and 1b, the 2D-detector 6 comprises an area 8 that extends beyond the multiple thickness degrader element 2 or beyond the wedge element 100, i.e. the surface of the 2D-detector 6 is larger than the surface 3 of the main degrader element. Because of this structural feature of the apparatus of the invention, it is possible to obtain measurements of pencil beams which are not passing through any degrader element. This means that with one measurement set-up (i.e. without having to replace the apparatus by another), a verification can be made of the beam range as described above, by pointing pencil beams at the main degrader element 1, and of the spot size and possibly also of the spot position and/or the spot fluence, by pointing pencil beams at the area 8. The spot size can be verified by comparing the measured spot to a prescribed spot size (as defined by a value known in the art, e.g. standard deviation (sigma) of a Gaussian distribution curve corresponding to the spot). To verify the beam position accuracy of the irradiation apparatus, the beam will be positioned to one or more prescribed positions. By comparing the actually measured positions and the prescribed positions, the positioning accuracy (elsewhere referred to as 'spot position') and reproducibility of the irradiation apparatus can be verified. As no degrader material is present above area 8, the 2D detector can also be used to determine the spot fluence or a signal that is proportional to the spot fluence, of a pencil beam directed at this area.

FIG. 4 shows a preferred embodiment of an apparatus of the invention, comprising three main degrader elements 30/31/32, each having the same square cross-section of 15×15 $cm^2$, each being arranged in contact with a multiple thickness degrader element 5 of the type shown in FIG. 2. The thickness of each main degrader element is chosen for a specific beam energy, for example degrader 30 is 275 mm (as in the previous example), degrader 31 is 190 mm and degrader 32 is 80 mm. The three main degrader elements and their respective multiple thickness degrader elements are arranged in three quadrants of a 30×30 $cm^2$ square, leaving one quadrant empty. In cooperation with the components shown in FIG. 4, a 2D-detector is mounted (not shown), extending underneath the three multiple thickness degrader elements and underneath the empty quadrant. This apparatus thus allows the verification of the beam range, the spot size and spot position for three distinct beam energies, by using the same verification setup. In the apparatus of FIG. 4, wedge degrader elements 100 can replace the multiple thickness patch degrader elements 5.

At the highest of the three beam energies, the apparatus of FIG. 4 allows a number of additional data points to be obtained in addition to points a to e, see FIG. 5:

Point g: measured by the detectors underneath the areas 10' (no patch) of the multiple thickness degrader element underneath the main degrader 32
Point h: measured by the 2D-detectors underneath the areas 10' (no patch) of the multiple thickness degrader element underneath the main degrader 31

Point i is measured by the detectors present underneath the empty quadrant.

Figure 6:
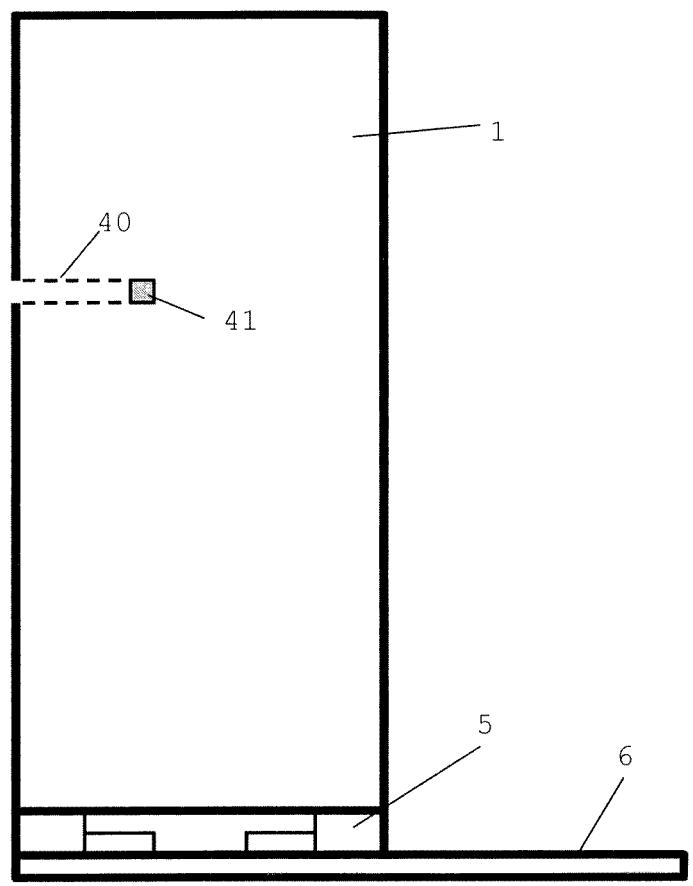
FIG. 6 shows an embodiment of the apparatus comprising an area for mounting an additional detector.

According to a specific embodiment, at least one of the main degrader elements 30/31/32, or 'the' main degrader element if only one such element is present (as in FIGS. 1a and 1b) is provided with a hole 40 in which a detector 41 can be placed for measuring the absolute deposited dose at the detector location. This is illustrated in FIG. 6 for an apparatus having one main degrader element. The absolute dose detector 41 is preferably an ionization chamber. The hole is made so as to be able to position the detector in the so-called 'plateau area' of the Bragg peak occurring in the degrader element. This plateau area is indicated as area 45 in FIG. 5. The measurement of the absolute dose at this position allows to verify the output factor of the irradiation installation during the daily check procedure. The output factor is a measure of the ratio of the delivered dose as measured by ionization chambers mounted at the outlet nozzle of the irradiation apparatus, to the dose actually reaching a given area in the target. The presence of an absolute dose measurement device thus allows to verify the output factor by the apparatus of the invention, together with the beam range verification and the spot size/spot position verification described above, without moving or replacing the apparatus.

Figure 7:
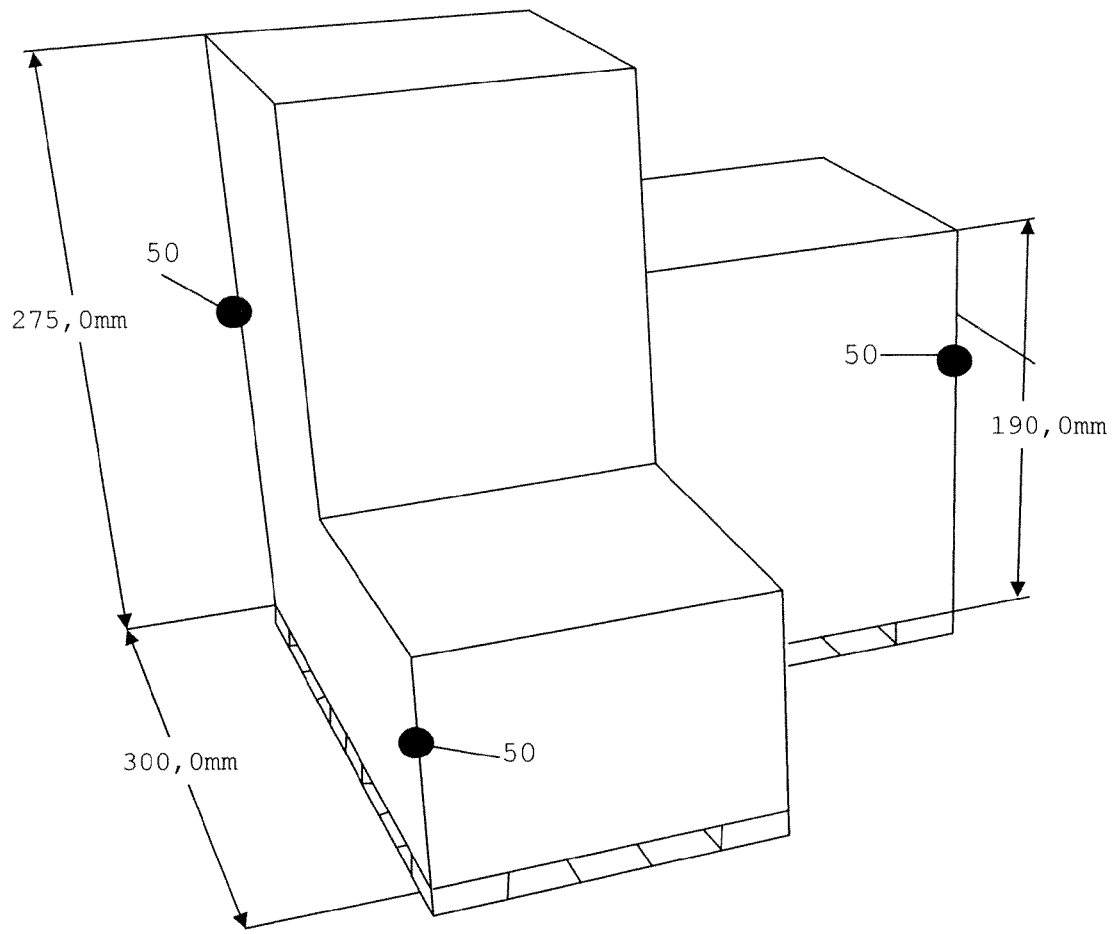
FIG. 7 is an embodiment of the apparatus comprising fiducials for X-ray calibration of the apparatus' position with respect to the irradiation device.

The apparatus of the invention is preferably mounted in a suitable frame or the like, which is configured to be mounted in the treatment room, at a fixed position with respect to the nozzle of the irradiation installation from which the beam is produced. In order to ensure that the position of the apparatus is repeated at every daily verification, the frame is preferably provided with mechanical clamping means which cooperate with matching clamping means, e.g. on the patient couch so that the frame can be secured into the same location at each verification procedure. In addition to this mechanical mounting mechanism, the position of the apparatus can be calibrated if the apparatus is provided with one or more X-ray identifiable targets as illustrated in FIG. 7. In the embodiment shown in that figure, these targets are small fiducials 50 attached at three positions of the apparatus, for example on the side ribs, as shown in the example. These fiducials allow to calibrate the position of the apparatus by taking an X-ray image of the apparatus under reference conditions, and comparing a daily X-ray of the apparatus to said reference image.

The use of an apparatus of the invention requires a specific irradiation schedule, adapted to the dimensions of the apparatus. For example in the case of the apparatus of FIG. 4, the irradiation schedule may comprise a predefined scanning pattern for sending the beam to different locations or spots in each quadrant of the 30×30 cm$^2$ square apparatus. According to one embodiment, the beam is directed to the centre of each of the patches 10 and empty areas 10' of the multiple thickness degrader elements 5. According to another embodiment, the beam is directed to multiple spots located on the patches 10 and empty areas 10', each spot being located at interdistances of 5 mm. In the second case, simulations have shown that the recorded dose remains essentially constant over the surface of a patch, except at the edges. It is therefore recommended not to irradiate spots that are within a border of about 10 mm from said edges. With an apparatus according to the invention, a morning check can be performed in 10-15 minutes: about 10 minutes would be required for positioning and securing the apparatus, and possibly fine-tuning the position through the X-ray calibration images. The running of the irradiation plan is possible in a time as short as 1 min, but may depend on the number of spots included in the plan. A suitable data processing scheme is then capable of outputting the required data (beam range, spot size, spot position, output factor) in a matter of seconds. The time required for running this procedure is therefore effectively shortened compared to the existing methods.

The shapes of the degrader elements are not limited to the shapes shown in the drawings. A main degrader element with a circular cross-section instead of a square cross-section could be used, combined with patches 10 of circular or square cross-section.

The order in which the main degrader element and the multiple thickness degrader element 5 or the wedge element 100 are placed with respect to the irradiation apparatus is not necessarily as shown in the drawings. The multiple thickness degrader element 5 or the wedge 100 may be placed before or after the main degrader element 1. This is illustrated in the case of the wedge in FIG. 8. Also, the wedge element may be integral with the main degrader element, as illustrated in FIG. 9. In the latter embodiment, a single degrader element 1' is used with non-parallel walls. Another embodiment (FIG. 10) has a combination of a first degrader element 200 with parallel walls and a second degrader element 201 with non-parallel walls. These embodiments illustrate that the 'main degrader element comprising two mutually parallel surfaces (2,3)' cited in the appended claims can either be a separate element, or it can be a portion of a larger element that encompasses the functions of the 'main' degrader element and a 'multiple thickness degrader element', the latter being provided with portions of different thickness.

Figure 11:
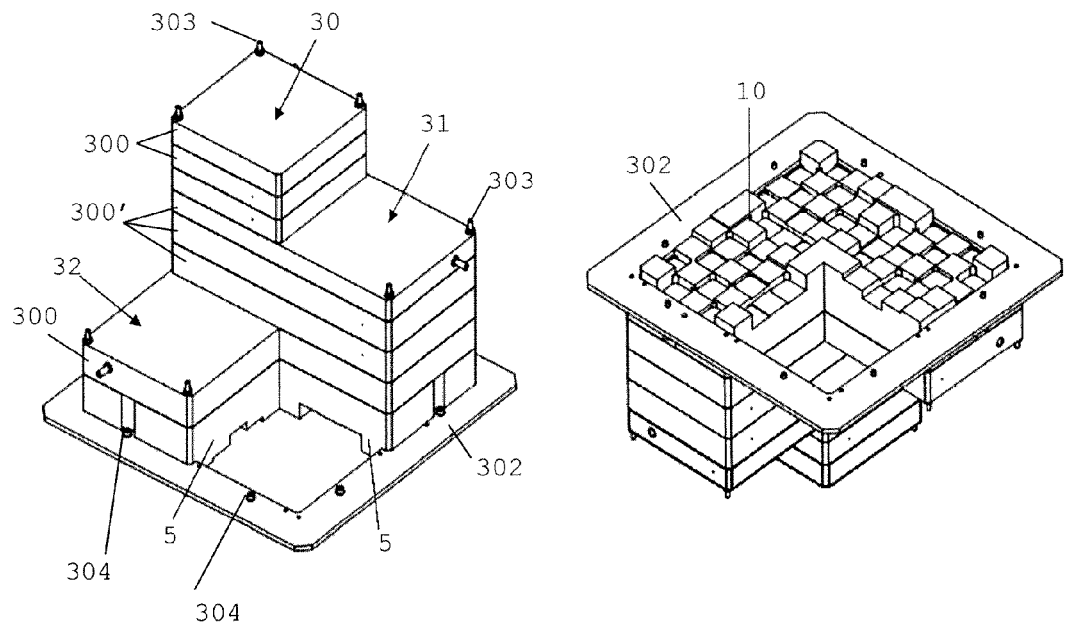
FIG. 11 shows a concrete embodiment of an apparatus of the invention comprising three distinct main degrader elements.
Figure 12:
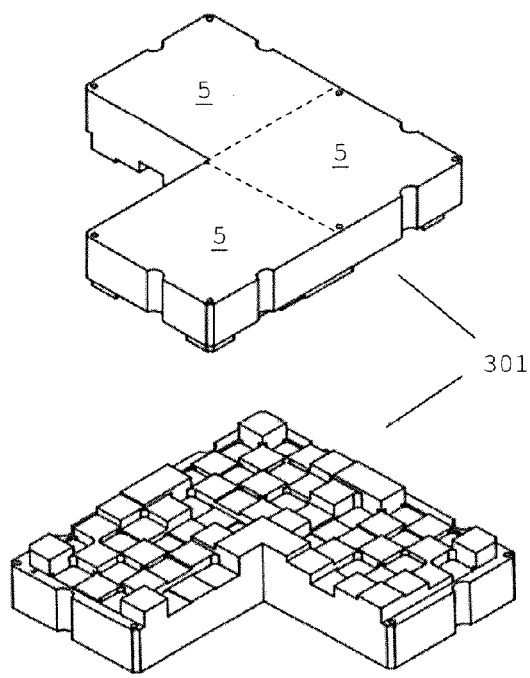
FIG. 12 shows an element comprising all three of the multiple thickness degrader elements used in the embodiment of FIG. 11.
Figure 13:
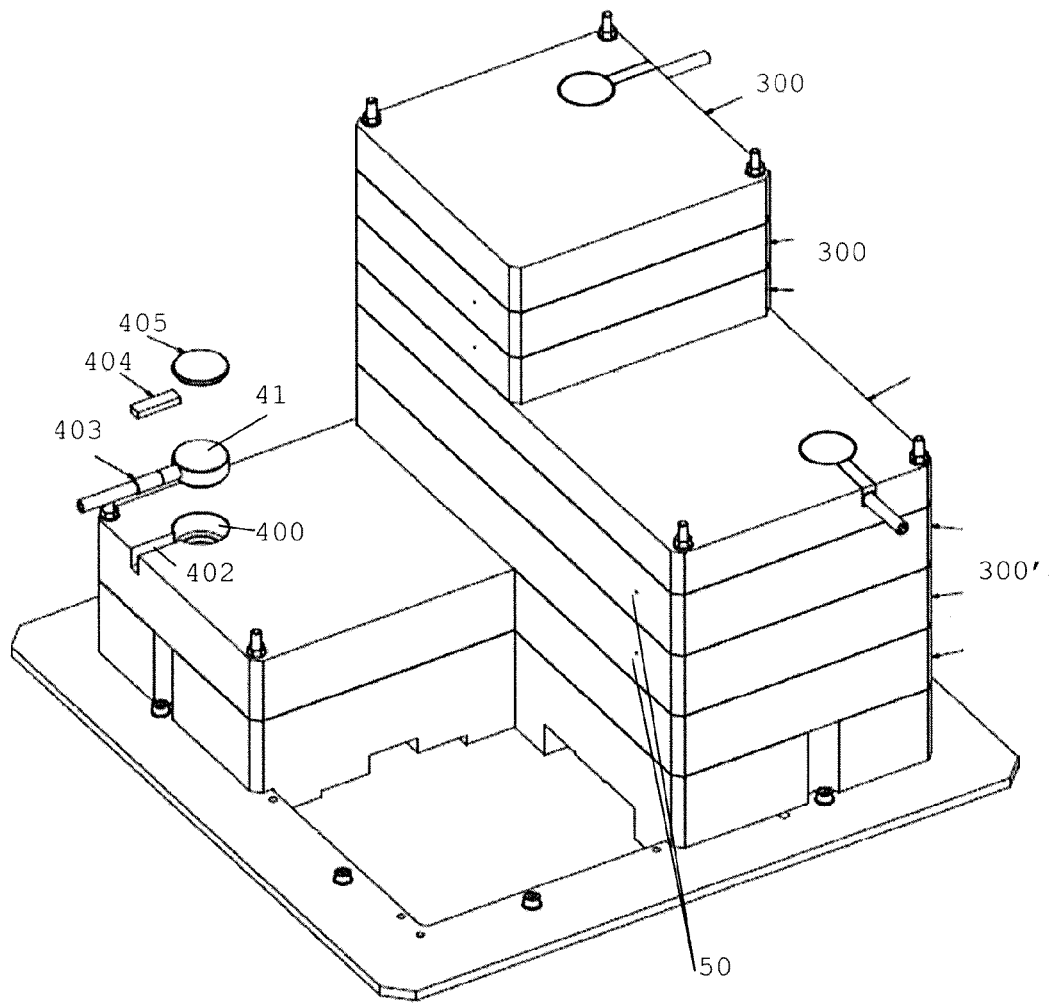
FIG. 13 illustrates the mounting of absolute dose detectors in the embodiment of FIG. 11.

FIGS. 11-13 illustrate a more concrete embodiment of the apparatus having three main degrader elements of different thickness. It is seen that the apparatus is modularly built: the main degrader elements 30 to 32 are built up from separate layers 300,300'. Layers that are common to two or three of the main degrader elements may be produced as integral pieces (such as the rectangular layers 300' that are common to the degrader elements 30 and 31). This structure allows to easily modify the thickness of the main degrader elements, by adding or removing layers from the structure. The multiple thickness degrader elements 5 equipped with constant thickness patches 10 are visible as well. In this embodiment, the three multiple thickness degrader elements 5 are formed by one integral piece 301, illustrated in FIG. 12. The various components of the structure are assembled to a carrier frame 302 via rods 303 passing through subsequent openings in the various layers 300. The rods are screwed into or otherwise attached to the frame 302, which is to be mounted on top of the 2D detector (not shown), attached thereto through positioning bolts 304. Exact positioning of the layers 300 with respect to the frame is obtained by positioning pins (not shown) mounted on the frame 302, and corresponding to positioning holes in the multiple thickness degrader element piece 301.

FIG. 13 illustrates a preferred way in which the absolute dose detector 41 can be mounted in this embodiment. In one of the layers, a recess 400 is formed, in which the detector 41 can be placed. A trench 402 is further provided for accommodating an output connector 403 issuing from the detector, while closing elements 404/405 are placed above the detector and its output connector. The fact that the opening 400 for mounting a detector is part of one of the layers 300 makes it easy to change the position of the detector by re-arranging the order of the layers. FIG. 13 also illustrates the previously described fiducials 50 for X-ray based calibration of the position of the apparatus.

Another way of describing the apparatus of the invention, including more explicit references to the functionality of a number of components is as follows: an apparatus for verification of characteristics of a pencil beam of a pre-defined beam energy, produced by a hadron beam irradiation installation, said pencil beam depositing a dose when travelling through matter, said dose following a characteristic Bragg curve having a Bragg peak where the dose deposit is at its maximum, the position of said peak determining the beam range of said pencil beam, said apparatus comprising:

A main degrader element (1) for reducing said beam range of said pencil beam, said main degrader element (1) comprising two mutually parallel surfaces (2,3), the distance between said surfaces defining the thickness of said main degrader element (1), Associated with said main degrader element, a multiple thickness degrader element (5), comprising a plurality of degrader portions of different thicknesses for further reducing the beam range of said pencil beam, each of said portions facing a different portion of the cross-section of one of said mutually parallel surfaces (2,3), A two-dimensional detection means (6), suitable for detecting a dose deposited by said pencil beam or a signal representative thereof or proportional thereto, wherein said detection means have a first portion (7) associated with said main and multiple thickness degrader elements (1,5), said first portion being configured to detect a dose signal of said pencil beam (4) when said beam has passed through said main degrader element (1) and through a degrader portion of said multiple thickness degrader element (5), the thickness of the main degrader element and of said plurality of degrader portions are configured to allow for measuring multiple data points of said Bragg peak, to thereby define the shape and position of said Bragg peak, said detection means further has a second portion (8) configured to detect pencil beams (4') that have not passed through said degrader elements.

Figure 14:
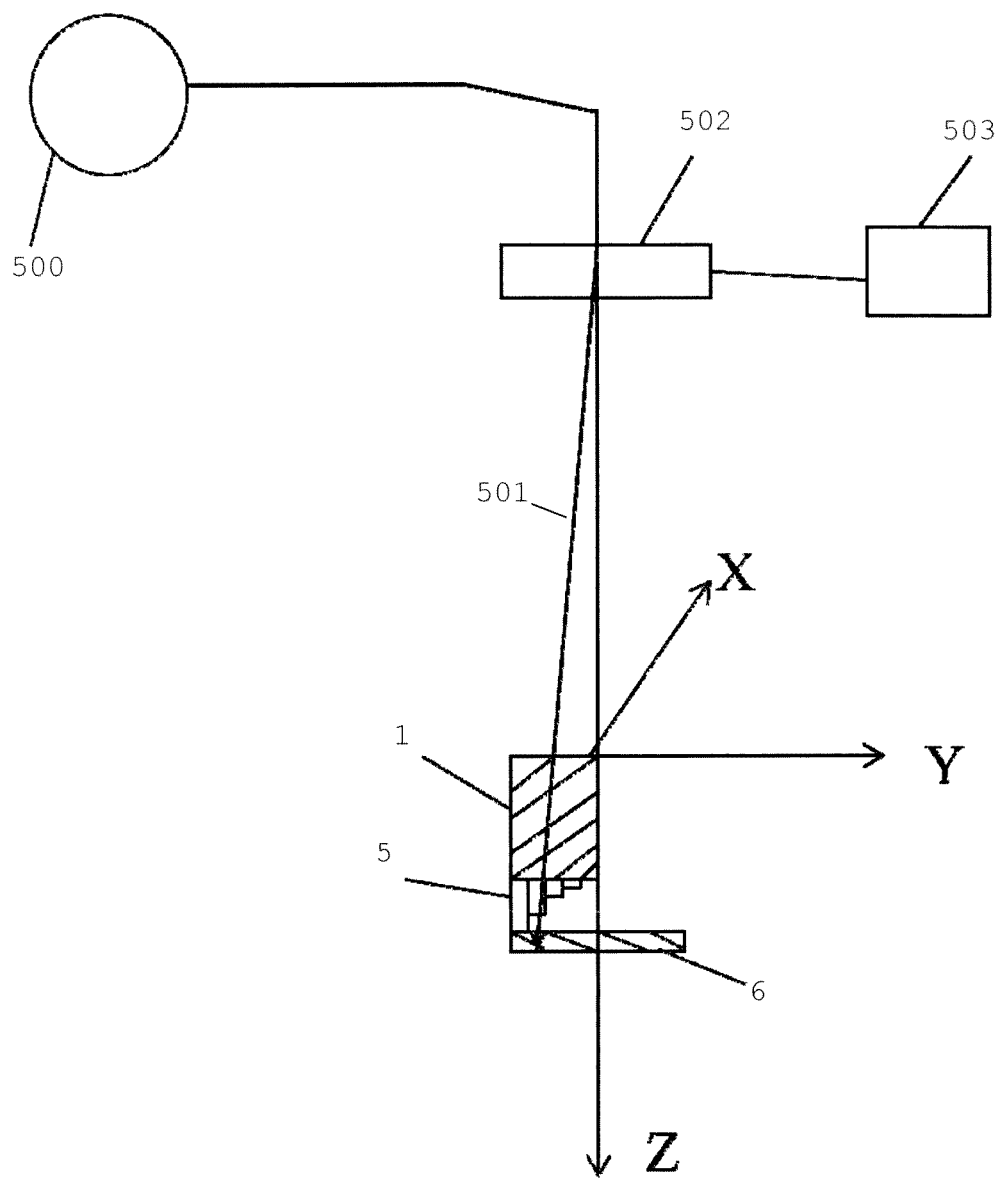
FIG. 14 illustrates a hadron therapy system for irradiating a target with a hadron pencil beam, according to the invention.

The invention is equally related to a hadron therapy system for irradiating a target with a hadron pencil beam. A system according to the invention is illustrated in FIG. 14, and comprises:

A hadron beam generator 500 for generating a hadron pencil beam;

a scanning device for scanning said target with said hadron pencil beam 501, said scanning device comprising:

one or more scanning magnets 502 configured for scanning the hadron pencil beam over an X-Y scanning plane, said scanning X-Y plane being perpendicular to an axis Z corresponding to a central beam path, said central beam path being the trajectory of the hadron pencil beam when all of said one or more scanning magnets are not energized;

scanning control means 503 configured for scanning the hadron pencil beam by sequentially moving the particle beam to multiple scanning positions situated in said X-Y scanning plane;

an apparatus for verification of characteristics of said pencil beam according the invention, comprising a main degrader element 1, a multiple thickness degrader element 5 and a 2D-detector 6, said apparatus being located such that said parallel surfaces 2,3 of said main degrader element 1 are essentially perpendicular to said axis Z.

In a preferred embodiment of the hadron therapy system according to the invention, each of said scanning positions is correlated either to one of said plurality of degrader portions or it is correlated to a location in said second portion of said two-dimensional detector. Being correlated to a portion or location means that the pencil beam is directed to one of said portions or locations.

While the invention has been illustrated and described in detail in the drawings and foregoing description, such illustration and description are to be considered illustrative or exemplary and not restrictive. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An apparatus for verification of characteristics of pencil beams produced by a hadron beam irradiation installation, comprising:

A main degrader element (1), comprising two mutually parallel surfaces (2,3), the distance between said surfaces defining the thickness of said main degrader element (1), Associated with said main degrader element, a multiple thickness degrader element (5), comprising a plurality of degrader portions of different thicknesses, each of said portions facing a different portion of the cross-section of one of said mutually parallel surfaces (2,3), A two-dimensional detection means (6), suitable for detecting a deposited dose or a signal representative thereof or proportional thereto, said detection means having a first portion (7) associated with said main and multiple thickness degrader elements (1,5), said first portion being configured to detect pencil beams (4) which have passed through said main degrader element (1) and said multiple thickness degrader element (5), wherein:

the thickness of said main degrader element (1) and the thickness of said degrader portions of the multiple thickness degrader element are designed with respect to a pre-defined beam energy, so as to obtain—through said first portion of the detection means—a plurality of data points in the vicinity of a Bragg peak appearing when a beam having said beam energy passes through said main degrader element, said two-dimensional detection means (6) comprises a second portion (8) configured to detect pencil beams (4') that have not passed through said degrader elements.

2. The apparatus according to claim 1, wherein said degrader portions are formed by a plurality of degrader patches (10) of different thicknesses, each patch having a constant thickness, said patches being positioned parallel to said mutually parallel surfaces (2,3) of the main degrader element (1).

3. The apparatus according to claim 2, wherein said multiple thickness degrader element (5) further comprises at least one area (10') where no degrader patch is present.

4. The apparatus according to claim 2, wherein all of said degrader patches (10), having a first and a second surface with said thickness being the distance between said surfaces, are arranged so that all of the first surfaces of each patch are in a single plane and all of the second surfaces of each patch are extending away from said plane.

5. The apparatus according to claim 1, wherein the main degrader element (1) and the multiple thickness degrader element (5) have the same rectangular cross-section along the direction of said mutually parallel surfaces (2,3), and wherein said patches (10) have rectangular sections along said direction.

6. The apparatus according to claim 1, wherein said multiple thickness degrader element is a wedge-shaped degrader element (100), said degrader portions being formed by cross-sections of the wedge-shaped element that have different thicknesses.

7. The apparatus according to claim 1, comprising a plurality of main degrader elements (30,31,32) of different thicknesses, each main degrader element being associated as in claim 1 with a multiple thickness degrader element (5,100), and wherein said two-dimensional detection means comprises portions associated with each of said main degrader elements as in claim 1, and further comprising said second portion configured to detect pencil beams (4') that have not passed through any of said degrader elements, wherein the thickness of each main degrader element is associated with a different pre-defined beam energy.

8. The apparatus according to claim 1, wherein said main degrader element (1) or at least one of said main degrader elements (30,31,32) comprises an area (40) wherein a detector (41) can be mounted suitable for determining the absolute dose deposited by a pencil beam aimed at said detector (41), and wherein said detector is positioned in the plateau area (45) of the Bragg peak occurring in said main degrader element.

9. The apparatus according to claim 1, further comprising a plurality of X-ray targets (50) suitable for establishing a reference position of the apparatus.

10. The apparatus according to claim 1, wherein said apparatus further comprises data treatment means and data representation means, suitable for receiving and treating signals obtained from the 2D-detector and to derive and present on the basis of those signals at least the following data:

the beam range, and the spot size or a parameter representative of said size.

11. The apparatus according to claim 1, wherein the main degrader element or elements is or are built up from separate layers (300,300').

12. The apparatus according to claim 11, wherein layers that are common to a plurality of main degrader elements are produced as integral pieces.

13. The apparatus according to claim 11, wherein one or more of said layers comprises an area (400) wherein a detector can be mounted suitable for determining the absolute dose deposited by a pencil beam aimed at said detector.

14. The apparatus according to claim 1, wherein the ratio between the thickness of the main degrader element and the highest thickness occurring in the multiple thickness degrader element is higher than 5.

15. A method for verifying characteristics of a pencil beam produced by a hadron beam irradiation installation, said method comprising the steps of:
   Positioning the apparatus of claim 1 at a predefined location with respect to a hadron beam irradiation nozzle, so that a pencil beam may be directed at the mutually parallel planes (2,3) of the main degrader element (1),
   Setting the hadron beam irradiation installation for delivering a pencil beam having an energy corresponding to the pre-defined energy for which the thickness of the main degrader element and the thickness of the degrader portions are designed,
   Producing said pencil beam,
   Sending said pencil beam in the direction of at least two of said plurality of degrader portions of different thickness, and detecting with the first portion (7) of said two-dimensional detection means (6) a plurality of data points in the vicinity of a Bragg peak appearing as a consequence of said beam passing through said main degrader element,
   Sending said pencil beam in the direction of one or more predefined spot locations on the second portion (8) of the two-dimensional detection means (6),
   Deriving from the obtained data at least:
      the beam range, and
      the spot size or a parameter representative of said size.

16. The method according to claim 15, wherein the step of positioning the apparatus includes placing the apparatus on a predefined position of a patient couch of a hadron therapy treatment room, and positioning the patient couch.

17. The method according to claim 15, further comprising the step of taking an X-ray image of the apparatus and positioning the apparatus by comparing the position of X-ray targets (50) in said X-ray image to a reference image.

18. A hadron therapy system for irradiating a target with a hadron pencil beam, said hadron therapy system comprising:
   A hadron beam generator for generating a hadron pencil beam;
   a scanning device for scanning said target with said hadron pencil beam, said scanning device comprising:
      one or more scanning magnets configured for scanning the hadron pencil beam over an X-Y scanning plane, said scanning X-Y plane being perpendicular to an axis Z corresponding to a central beam path, said central beam path being the trajectory of the hadron pencil beam when all of said one or more scanning magnets are not energized;
      scanning control means configured for scanning the hadron pencil beam by sequentially moving the particle beam to multiple scanning positions situated in said X-Y scanning plane;
   an apparatus for verification of characteristics of said pencil beam according to any of previous claims, said apparatus being located such that said parallel surfaces of said main degrader element are essentially perpendicular to said axis Z.

19. A hadron therapy system according to claim 18, wherein each of said scanning positions is correlated either to one of said plurality of degrader portions or it is correlated to a location in said second portion of said two-dimensional detector.

* * * * *